United States Patent
Morris et al.

(10) Patent No.: US 8,912,225 B2
(45) Date of Patent: Dec. 16, 2014

(54) VEGF INHIBITION

(75) Inventors: David L. Morris, Lugarno (AU); Mohammad H. Pourgholami, Penshurst (AU)

(73) Assignee: Pitney Pharmaceuticals Pty Limited, Sydney, NSW (AU)

( * ) Notice: Subject to any disclaimer, the term of this patent is extended or adjusted under 35 U.S.C. 154(b) by 1804 days.

(21) Appl. No.: 11/661,460

(22) PCT Filed: Aug. 31, 2005

(86) PCT No.: PCT/AU2005/001318
§ 371 (c)(1),
(2), (4) Date: Oct. 23, 2008

(87) PCT Pub. No.: WO2006/024092
PCT Pub. Date: Mar. 9, 2006

(65) Prior Publication Data
US 2009/0105317 A1   Apr. 23, 2009

(30) Foreign Application Priority Data
Aug. 31, 2004 (AU) ................................ 2004904972
Aug. 31, 2004 (AU) ................................ 2004904973

(51) Int. Cl.
*A61K 31/415* (2006.01)
*A61K 31/4184* (2006.01)
*A61K 31/427* (2006.01)

(52) U.S. Cl.
CPC ........... *A61K 31/427* (2013.01); *A61K 31/4184* (2013.01)
USPC .......................................... 514/398; 514/396

(58) Field of Classification Search
USPC ................................................. 514/365, 394
See application file for complete search history.

(56) References Cited

U.S. PATENT DOCUMENTS

| 6,342,219 B1 * | 1/2002 | Thorpe et al. ............... 424/145.1 |
| 6,693,125 B2 * | 2/2004 | Borisy et al. ................... 514/388 |
| 2002/0165261 A1 * | 11/2002 | Borisy et al. ................... 514/394 |

FOREIGN PATENT DOCUMENTS

| CA | 2342470 A1 * | 9/2002 | |
| EP | 1 197 223 B1 | 2/2005 | |
| JP | 2002-193947 | 7/2002 | |
| JP | 2002193947 * | 6/2010 | ........... A61K 31/418 |
| WO | WO00/41669 A2 | 7/2000 | |
| WO | WO02/067932 A1 | 9/2002 | |
| WO | WO02/076454 | 10/2002 | |
| WO | WO2006/024092 A1 | 3/2006 | |

OTHER PUBLICATIONS

Appelqvist et al. "On the treatment and prognosis of malignant ascites: Is the survival time determined when the abdominal paracentesis is needed?" Journal of Surgical Oncology, 1982, vol. 20, pp. 238-242.*

Ozols et al., "Inhibition of Human Ovarian Cancer Colony Formation by Adriamycin and its Major Metabolites," 1980, Cancer Research, 40, pp. 4109-4112.

(Continued)

*Primary Examiner* — Shengjun Wang
(74) *Attorney, Agent, or Firm* — Kilpatrick Townsend & Stockton LLP

(57) ABSTRACT

The present invention provides methods for inhibiting VEGF production or secretion in a subject comprising administering to the subject an effective amount of a compound of Formula I. The invention also provides methods for the treatment or prevention of conditions associated with abnormal levels of VEGF production or secretion.

2 Claims, 10 Drawing Sheets

(56) References Cited

OTHER PUBLICATIONS

Amano et al., "Angiotensin II Stimulates Platelet-Derived Growth Factor-B Gene Expression in Cultured Retinal Pericytes through Intracellular Reactive Oxygen Species Generation", *International J. Tissue Reactions* 25(2):51-55 (2003).

De Brabander et al., "The Effects of Methyl (5-(2-thienylcarbonyl)-1H-benzimidazol-2-yl) carbamate, (R 17934; NSC238159), a New Synthetic Antitumoral Drug Interfering with Microtubules, on Mammalian Cell Cultured in Vitro" *Cancer Res.* 36:905-916 (1976).

Hong et al., "A Case of Gastroenteritis Associated with gastric Trichuriasis", *J. Korean Med. Sci.* 18(3):429-432 (2003).

Jesmin et al., "Role of ANG II in Coronary Capillary Angiogenesis at the Insulin-Resistant Stage of a NIDDM Rat Model", *Amer. J. Physiol. Heart and Circulatory Physiol.* 283(4):H1387-H1397 (2002).

Morris et al., "Pilot Study of Albendazole in Patients with Advanced Malignancy", *Oncology* 61:42-46 (2001).

Nagisa et al., "The Angiotensin II Receptor Antagonist Candesartan Cilexextil (TCV-116) Ameliorates Retinal Disorders in Rats" *Diabetoloia* 44:883-888 (2001).

Pourgholami et al., "Albendazole: a Potent Inhibitor of Vascular Endothelial Growth Factor and Malignant Ascites Formation in OVCAR-3 Tumor-Bearing Nude Mice", *Clin. Cancer Res.* 12(6):1928-1935 (2006).

Pourgholami et al., "In Vitro Inhibition of Human Liver Cancer Cells by Albendazole", *PNAS* 41:656 (2000) (Abstract).

Sjølie et al., "The Retinal Renin-Angiotensin system: Implications for Therapy in Diabetic Retinopathy", *J. Human Hypertension* 16(3):42-46 (2002).

Xu et al., "Inhibition of Malignant Ascites and Growth of Human Ovarian Carcinoma by Oral Administration of a Potent Inhibitor of the Vascular Endothelial Growth Factor Receptor Tyrosine Kinases", Medline Abstract, Accession No. 10675474. *International J. Oncology* 16(3):445-454 (2000) (Abstract).

Zebrowski et al., "Markedly elevated Levels of Vascular Endothelial Growth Factor in Malignant Ascites", *Ann. Surgical Oncology* 6(4):373-378 (1999).

Zebrowski et al., "Vascular Endothelial Growth Factor Levels and Induction of Permeability in Malignant Pleural Effusions", *Clin. Cancer Res.* 5(11):3364-3368 (1999).

Application No. EP 05776195.9, Supplementary European Search Report mailed May 7, 2009.

Application No. PCT/AU05/001318, International Search Report mailed Oct. 10, 2005.

* cited by examiner

VEGF INHIBITION

REFERENCE TO A "SEQUENCE LISTING", A TABLE, OR A COMPUTER PROGRAM LISTING

The Sequence Listing written in file SEQLIST083900000600US.txt is 1,168 bytes, and was created on Oct. 15, 2008, for Application Ser. No. 11/661,460, Morris et al, entitled "VEGF INHIBITION". The information contained in this file is hereby incorporated by reference.

TECHNICAL FIELD

In general, the present invention relates to methods for the treatment of conditions associated with abnormal levels of VEGF production and/or secretion.

BACKGROUND OF THE INVENTION

Vascular endothelial growth factor [VEGF; also known as vascular permeability factor (VPF)] is a highly conserved, potent multifunctional cytokine. Abnormal levels of production and or secretion of VEGF have been linked to a number of pathological conditions. For example, high concentrations of biologically active VEGF have been detected in pleural fluids and ascites of cancer patients (Zebrowski et al., 1999a, b).

Ascites, the accumulation of fluid in the abdominal cavity, may result from a number of conditions, including tumours and other disease states such as chronic liver disease. Cirrhosis of the liver is responsible for the majority of cases of ascites and the prognosis is generally poor.

Accumulation of malignant ascites is an important cause of morbidity and mortality in patients with peritoneal carcinomatosis. Causes of malignant ascites formation include colon, gastric, pancreatic, endometrial and ovarian cancer (Smith and Jayson, 2003). For example, the malignant progression of ovarian cancer is predominantly confined to the peritoneal cavity and often evolves to an ascites form (Ozols et al., 1980). Both tumour size and the accumulation of ascites are inversely associated with survival (Hasumi et al., 2002). Current therapeutic treatment of patients with advanced ovarian cancer associates cytoreductive surgery and systemic chemotherapy, the combination of paclitaxel and cisplatin being considered the initial chemotherapy for stage III and IV (Burbridge et al., 1999). However two thirds of patients already have advanced disease when diagnosed, and poor prognoses are associated with rapidly accumulating ascites fluid and highly invasive and pleomorphic cellular phenotypes. There remains a need for an effective method for the treatment of ascites and ascites-associated conditions.

Ascites is linked to peritoneal, as well as tumour microvascular hyperpermeability and several studies have implicated a role for VEGF in ascites formation via increasing vascular permeability. More generally, VEGF exerts a number of important effects on vascular endothelium including inducing new vascular formation. VEGF possesses potent vascular permeability-enhancing activity and abnormal levels of VEGF production or secretion lead to microvascular hyperpermeability. VEGF is now recognized as a key factor required for growth of tumours and is involved in many other disease states such as diabetes, arthritis including rheumatoid arthritis, psoriasis, endometriosis, cerebral oedema, atheroscelrosis, ischaemic heart disease, and retinopathic diseases such as age related macular degeneration.

Tumour secretion of VEGF is essential for ascites accumulation. Tumour cells usually represent the main source of VEGF, but tumour-associated stroma is also an important site of VEGF production. Blocking VEGF production or secretion by tumour cells, for example using a VEGF inhibitor, has been shown in animal studies to result in inhibition of ascites formation (Zebrowski et al., 1999a, b; Xu et al., 2000). There is also growing evidence that VEGF production and secretion is not limited to solid tumours, but that VEGF and VEGF receptors are expressed by a variety of leukemias and other haematological malignancies.

Accordingly, VEGF is an attractive target for therapeutic intervention and several strategies to block VEGF activity have been sought, including monoclonal antibodies, VEGF receptor antagonists, tyrosine kinase antagonists and soluble VEGF receptors (VEGF-trap). There remains a need however for an effective method of inhibiting VEGF production and/or secretion and for treatment of conditions associated with VEGF production and/or secretion.

The present invention is predicated on the inventors' surprising finding that the benzimidazole carbamate albendazole has a potent effect on VEGF levels secreted by human ovarian cancer cells in vitro and on VEGF levels in vivo, and exhibits significant inhibitory effect on a number of conditions associated with abnormal VEGF levels.

SUMMARY OF THE INVENTION

According to a first aspect of the present invention there is provided a method for inhibiting VEGF production or secretion in a subject, the method comprising administering to the subject an effective amount of a compound of Formula I:

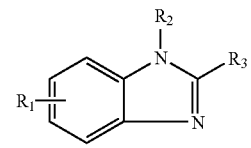

I wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, $-SR_7$, $-SOR_8$, $-SO_2R_9$, $-SCN$, $B'(CH_2)_nBR_{10}$, $-C(O)-R_{11}$ or $-OR_{12}$, $COOR_{13}$, $-NO_2$, $NR_{13a}COOR_{13b}$, isothiocyanato, or $-CN$ where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, $-SR_{14}$, $-OR_{15}$, $-SOR_{16}$, $-SO_2R_{17}$, $-SCN$, $-C(O)-R_{18}$, $-OR_{19}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl;

or a metabolite, derivative or analogue thereof.

In one embodiment the $R_1$ substitution occurs in the 5 or 6 position.

The compound may be a benzimidazole carbamate of Formula II:

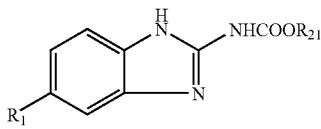

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_{21}$ is H, substituted or unsubstituted, straight or branch chain alkyl, alkenyl, alkenylalkyl, cycloalkyl, cycloalkylalkyl, cycloakenylalkyl, aryl or arylalkyl.

The compound may be a compound of Formula III:

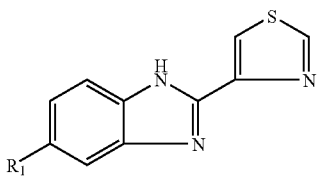

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4.

The compound may be selected from the group consisting of albendazole, albendazole sulphoxide, mebendazole, flubendazole, triclabendazole, oxfenbendazole, luxabendazole, cambendazole, oxibendazole, parbendazole, thiabendazole, cyclobendazole, dribendazole, etibendazole and fenbendazole.

In one embodiment the compound is albendazole, or a metabolite, derivative or analogue thereof.

The VEGF may be produced or secreted by a tumour cell. The tumour cell may be an ovarian, colorectal, liver, pancreatic, gastric, endometrial, renal or other primary or metastatic tumour cell.

The VEGF production or secretion may be associated with an accumulation of fluid in a body cavity, such as ascites or pleural effusion.

The VEGF production or secretion may be associated with retinopathic neovascularisation, such as in proliferative retinopathy or macular degeneration.

According to a second aspect of the present invention there is provided a method for treating or preventing a condition associated with abnormal levels of production or secretion of VEGF in a subject, the method comprising administering to the subject an effective amount of a compound of Formula I:

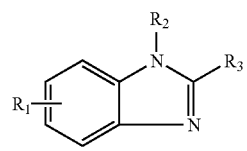

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —$SR_{14}$, —$OR_{15}$, —$SOR_{16}$, —$SO_2R_{17}$, —SCN, —C(O)—$R_{18}$, —$OR_{19}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl;

or a metabolite, derivative or analogue thereof.

In one embodiment the compound is albendazole, or a metabolite, derivative or analogue thereof.

The condition may be one associated with increased vascular permeability. The condition may be selected from the group consisting of: ascites, cirrhosis, pleural effusion, cerebral oedema, pulmonary oedema, ischaemic heart disease, macular degeneration, proliferative retinopathy, diabetic retinopathy, retinopathy of prematurity, psoriasis, endometriosis and arthritis, such as rheumatoid arthritis.

Administration of the compound may be systemic or regional depending on the nature of the condition to be treated. Administration may be intracavitary, intravesical, intramuscular, intraarterial, intravenous, subcutaneous, topical or oral. Intracavitary administration may be intraperitoneal or intrapleural.

According to a third aspect of the present invention there is provided a method for the treatment or prevention of ascites or an ascites-associated condition in a subject, the method comprising administering to the subject an effective amount of a compound of Formula I:

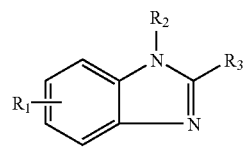

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —$SR_{14}$, —$OR_{15}$, —$SOR_{16}$, —$SO_2R_{17}$, —SCN, —C(O)—$R_{18}$, —$OR_{19}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl;

or a metabolite, derivative or analogue thereof.

In one embodiment the compound is albendazole, or a metabolite, derivative or analogue thereof.

The ascites may be malignant ascites. The ascites-associated condition may be cirrhosis.

The compound may be administered systemically or regionally. The compound may be administered intraperitoneally.

According to a fourth aspect of the present invention there is provided a method for the treatment or prevention of a retinopathic disease in a subject, the method comprising administering to the subject an effective amount of a compound of Formula I:

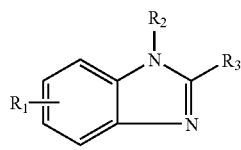

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, $B'(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —$SR_{14}$, —$OR_{15}$, —$SOR_{16}$, —$SO_2R_{17}$, —SCN, —C(O)—$R_{18}$, —$OR_{19}$, $NR_{20}COOR_{21}$, where $R_{15}$ to $R_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl;

or a metabolite, derivative or analogue thereof.

In one embodiment the compound is albendazole, or a metabolite, derivative or analogue thereof.

The retinopathic disease may be selected from proliferative retinopathy, diabetic retinopathy, retinopathy of prematurity or macular degeneration.

According to any one of the above aspects and embodiments the compound may be administered in the form of a composition together with one or more pharmaceutically acceptable carriers, adjuvants or diluents.

According to a fifth aspect of the present invention there is provided a composition when used for inhibiting VEGF production or secretion by a cell, wherein the composition comprises a compound of Formula I together with one or more pharmaceutically acceptable carriers, diluents or adjuvants.

According to a sixth aspect of the present invention there is provided a composition when used for the treatment or prevention of ascites or an ascites-associated condition, wherein the composition comprises a compound of Formula I together with one or more pharmaceutically acceptable carriers, diluents or adjuvants.

According to a seventh aspect of the present invention there is provided a composition when used for the treatment or prevention of a retinopathic disease, wherein the composition comprises a compound of Formula I together with one or more pharmaceutically acceptable carriers, diluents or adjuvants.

According to an eighth aspect of the present invention there is provided a composition when used for the treatment or prevention of a condition associated with VEGF production or secretion, wherein the composition comprises a compound of Formula I together with one or more pharmaceutically acceptable carriers, diluents or adjuvants.

According to a ninth aspect of the present invention there is provided a method for designing a benzimidazole carbamate treatment regime for a subject, comprising monitoring the serum VEGF concentration in the subject in the presence and absence of one or more candidate benzimidazole carbamates and adjusting the identity and/or dosage of the benzimidazole carbamates so as to achieve a reduction in serum VEGF concentration.

According to a tenth aspect there is provided a method for treating a subject in need of treatment using a benzimidazole carbamate treatment regime designed according to the ninth aspect.

Also contemplated within the above aspects and embodiments are isomers, including stereoisomers and geometric isomers of the compounds of Formula I, II and III, as well as tautomeric forms thereof.

Definitions

In the context of this specification, the term "comprising" means "including principally, but not necessarily solely". Furthermore, variations of the word "comprising", such as "comprise" and "comprises", have correspondingly varied meanings.

The term "inhibiting" as used herein in relation to VEGF levels means preventing, reducing or otherwise ameliorating VEGF production or secretion. For example, depending on the circumstances, including the nature of the condition being treated, it may not be necessary that inhibition should mean completely blocking VEGF production or secretion, but reducing VEGF production to a sufficient degree to enable the desired effect to be achieved.

As used herein the terms "treating" and "treatment" refer to any and all uses which remedy a condition or symptoms, prevent the establishment of a condition or disease, or otherwise prevent, hinder, retard, or reverse the progression of a condition or disease or other undesirable symptoms in any way whatsoever.

The term "ascites-associated condition" as used herein refers to a condition associated with, at least in part, the accumulation of excess fluid in the abdominal cavity. The condition may be characterized by such accumulation, may occur as a result, either directly or indirectly, of such accumulation or itself lead to the accumulation of excess fluid in the abdominal cavity. One exemplary ascites-associated condition is cirrhosis.

As used herein the term "effective amount" includes within its meaning a non-toxic but sufficient amount of an agent or compound to provide the desired effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

The term "alkyl" as used herein, includes within its meaning monovalent, saturated, straight and branched chain hydrocarbon radicals.

The term "alkenyl" as used herein, includes within its meaning, monovalent, straight and branched chain hydrocarbon radicals having at least one double bond.

The term "aryl" as used herein, includes within its meaning monovalent, single, polynuclear, conjugated and fused aromatic hydrocarbon radicals.

BRIEF DESCRIPTION OF THE DRAWINGS

The present invention will now be described, by way of example only, with reference to the following drawings.

BEST MODE OF PERFORMING THE INVENTION

Figure 1:
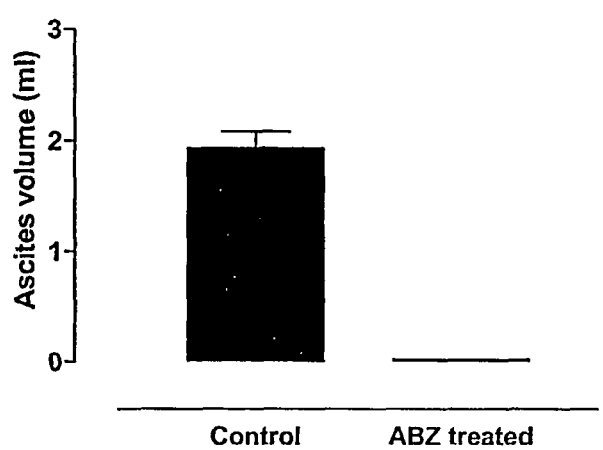
FIG. 1. Effect of intraperitoneal albendazole treatment (150 mg/kg×3 weekly for 4 weeks) on ascites production in nude mice bearing peritoneal OVCAR-3 tumours. Ascites fluid volume (ml) in control and albendazole (ABZ) treated mice. Each value represents the mean±s.e. of 6 to 8 determinations.

Benzimidazole carbamate compounds are broad-spectrum anthelmintic drugs, widely used for the control of helminth parasites in mammals, including humans. The primary target of benzimidazole carbamates is believed to be tubulin, the compounds acting to inhibit tubulin polymerization and destabilize microtubules. One such benzimidazole carbamate is albendazole (methyl 5-propylthio-IH-benzimidazole-2-yl carbamate). Other benzimidazole carbamates include mebendazole, flubendazole, triclabendazole, oxfenbendazole, luxabendazole, cambendazole, oxibendazole, parbendazole, thiabendazole, cyclobendazole, dribendazole, etibendazole and fenbendazole.

The present inventors have previously found that albendazole has an anti-proliferative effect on a range of cancer cell lines in vitro and on cancers in animal models and clinical studies (WO 02/076454, the disclosure of which is incorporated herein by reference). As disclosed herein, the present inventors have now demonstrated that albendazole has a potent effect on VEGF levels secreted by human ovarian cancer cells in vitro, on ascites production, retinal neovascularisation and on VEGF levels in vivo.

Accordingly, one aspect of the present invention relates to a method for inhibiting VEGF production or secretion by a cell in a subject, the method comprising administering to the subject an effective amount of a compound of Formula I:

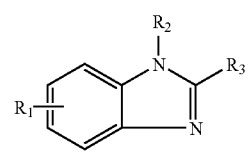

wherein $R_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —$SR_7$, —$SOR_8$, —$SO_2R_9$, —SCN, B'$(CH_2)_nBR_{10}$, —C(O)—$R_{11}$ or —$OR_{12}$, $COOR_{13}$, —$NO_2$, $NR_{13a}COOR_{13b}$, isothiocyanato, or —CN where $R_7$ to $R_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or $SO_2$ and n is 1 to 4;

$R_2$ is selected from H, or substituted or unsubstituted alkyl;

$R_3$ is selected from H, substituted or unsubstituted, straight or branch chain alkyl, alkenyl, alkenylalkyl, cycloalkyl, cycloalkylalkyl, cycloalkenylalkyl, aryl, arylalkyl, 5- or 6-membered heterocyclic ring the heteroatom(s) of which are selected from one or more of O, S and/or N, —SR$_{14}$, —OR$_{15}$, —SOR$_{16}$, —SCN, —SO$_2$R$_{17}$, —C(O)—R$_{18}$, —OR$_{19}$, NR$_{20}$COOR$_{21}$, where R$_{15}$ to R$_{21}$ are each independently selected from H, substituted or unsubstituted, straight or branch chain alkyl, alkenyl, alkenylalkyl, cycloalkyl, cycloalkylalkyl, cycloalkenylalkyl, aryl or arylalkyl; or an analogue, metabolite or derivative thereof.

Typically the compound is a benzimidazole carbamate of formula II

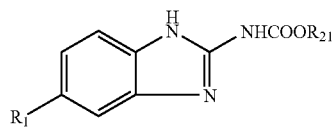

II wherein R$_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —SR$_7$, —SOR$_8$, —SO$_2$R$_9$, —SCN, B'(CH$_2$)$_n$BR$_{10}$, —C(O)—R$_{11}$ or —OR$_{12}$, COOR$_{13}$, —NO$_2$, NR$_{13a}$COOR$_{13b}$, isothiocyanato, or —CN where R$_7$ to R$_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or SO$_2$ and n is 1 to 4;

R$_{21}$ is H, substituted or unsubstituted, straight or branch chain alkyl, alkenyl, alkenylalkyl, cycloalkyl, cycloalkylalkyl, cycloakenylalkyl, aryl or arylalkyl, or of formula III

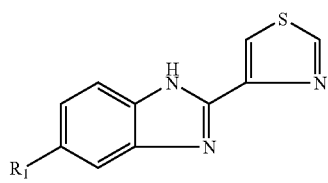

III wherein R$_1$ is selected from H, substituted or unsubstituted, straight or branch chain alkyl, alkenyl, alkenylalkyl, cycloalkyl, cycloalkylalkyl, cycloalkenylalkyl, aryl, arylalkyl, —SR$_7$, —SOR$_8$, —SO$_2$R$_9$, —SCN, B'(CH$_2$)$_n$BR$_{10}$, —C(O)—R$_{11}$ or —OR$_{12}$, COOR$_{13}$, —NO$_2$, NR$_{13a}$COOR$_{13b}$, isothiocyanato, or —CN where R$_7$ to R$_{13b}$ are each independently selected from H, substituted or unsubstituted, straight or branch chain alkyl, alkenyl, alkenylalkyl, cycloalkyl, cycloalkylalkyl, cycloalkenylalkyl, aryl, arylalkyl, B and B' are independently selected from O, S, S(O) or SO$_2$ and n is 1 to 4.

Those skilled in the art will readily appreciate that isomers, including stereoisomers and geometric isomers, of the above described compounds may exists and the use of such isomers are included within the scope of the present invention. Further, the use of tautomeric forms of the above compounds is also contemplated. For example the substituted benzimidazole group may exist in a number of tautomeric forms, including where the R$_1$ substituent is in any one of the 4 to 7 positions.

Albendazole or a metabolite, derivative or analogue thereof (such as albendazole sulphoxide or albendazole sulfone) is one bezimidazole carbamate particularly useful in methods and compositions of the present invention. However it will be readily appreciated by those skilled in the art that other bezimidazole carbamates may also be employed. For example other suitable bezimidazole carbamates include, but are not limited to, mebendazole, flubendazole, triclabendazole, oxfenbendazole, luxabendazole, cambendazole, oxibendazole, parbendazole, thiabendazole, cyclobendazole, dribendazole, etibendazole and fenbendazole.

Conditions

A compound as described above may act to inhibit the cellular production of VEGF and/or may inhibit secretion of VEGF from cells in the subject undergoing treatment. Accordingly, the present invention provides methods and compositions for the treatment or prevention of conditions associated with abnormal, typically increased, levels of VEGF production or secretion, including conditions associated with increased vascular permeability, using such compounds as described above. Conditions to which methods and compositions of the invention are applicable include, but are not limited to, ascites, cirrhosis and other ascites-associated conditions, pleural effusion, cerebral oedema, pulmonary oedema, ischaemic heart disease, macular degeneration such as age-related macular degeneration, proliferative retinopathy, diabetic retinopathy, retinopathy of prematurity psoriasis, endometriosis and arthritis, such as rheumatoid arthritis.

The inventors' findings as disclosed herein demonstrate that intra-peritoneal administration of albendazole rapidly reduces serum VEGF levels. Thus, the monitoring of serum VEGF levels will enable the design and implementation of appropriate benzimidazole carbamate therapy for patients in need of such therapy. Accordingly, an embodiment of the present invention provides a method for designing a benzimidazole carbamate treatment therapy for a subject, comprising monitoring the serum VEGF concentration in the subject in the presence and absence of one or more candidate benzimidazole carbamates and adjusting the identity and/or dosage of the benzimidazole carbamates so as to achieve a reduction in tumour or serum VEGF concentration.

Compositions and Routes of Administration

Embodiments of the present invention contemplate compositions for inhibiting VEGF production or secretion in a subject and for treating or preventing a condition associated with abnormal levels of production or secretion of VEGF.

According to the methods of present invention compounds and compositions may be administered by any suitable route, either systemically, regionally or locally. The particular route of administration to be used in any given circumstance will depend on a number of factors, including the nature of the condition to be treated, the severity and extent of the condition, the required dosage of the particular compound to be delivered and the potential side-effects of the compound.

For example, in circumstances where it is required that appropriate concentrations of the desired compound are delivered directly to the site in the body to be treated, administration may be regional rather than systemic. Regional administration provides the capability of delivering very high local concentrations of the desired compound to the required site and thus is suitable for achieving the desired therapeutic or preventative effect whilst avoiding exposure of other organs of the body to the compound and thereby potentially reducing side effects.

By way of example, administration according to embodiments of the invention may be achieved by any standard routes, including intracavitary, intravesical, intramuscular, intraarterial, intravenous, intraocular, subcutaneous, topical or oral. Intracavitary administration may be intraperitoneal or intrapleural. For example, in the treatment of ascites the desired compound may be administered intra-peritoneally and for the treatment of pleural effusion administration may be intra-pleural.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions.

For administration as an injectable solution or suspension, non-toxic parenterally acceptable diluents or carriers can include, Ringer's solution, medium chain triglyceride (MCT), isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

Compounds and compositions disclosed herein may be administered either therapeutically or preventively. In a therapeutic application, compounds and compositions are administered to a, patient already suffering from a condition, in an amount sufficient to cure or at least partially arrest the condition and its symptoms and/or complications. The compound or composition should provide a quantity of the active compound sufficient to effectively treat the patient.

The effective dose level of the administered compound for any particular subject will depend upon a variety of factors including: the type of condition being treated and the stage of the condition; the activity of the compound employed; the composition employed; the age, body weight, general health, sex and diet of the patient; the time of administration; the route of administration; the rate of sequestration of compounds; the duration of the treatment; drugs used in combination or coincidental with the treatment, together with other related factors well known in medicine.

One skilled in the art would be able, by routine experimentation, to determine an effective, non-toxic dosage which would be required to treat applicable conditions. These will most often be determined on a case-by-case basis.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range of about 10 mg to about 200 mg per kg body weight per 24 hours.

Alternatively, an effective dosage may be up to about 5000 mg/m$^2$. Generally, an effective dosage is expected to be in the range of about 10 to about 5000 mg/m$^2$, typically about 10 to about 2500 mg/m$^2$, about 25 to about 2000 mg/m$^2$, about 50 to about 1500 mg/m$^2$, about 50 to about 1000 mg/m$^2$, or about 75 to about 600 mg/m$^2$.

Further, it will be apparent to one of ordinary skill in the art that the optimal quantity and spacing of individual dosages will be determined by the nature and extent of the condition being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

The present invention will now be further described in greater detail by reference to the following specific examples, which should not be construed as in any way limiting the scope of the invention.

EXAMPLES

Example 1

Albendazole Treatment of OVCAR-3 Peritoneal Tumour Bearing Nude Mice

Cells of the cell line NIH:OVCAR-3 (ATCC Accession No. HTB 161) have the capacity to grow intra-peritoneally in female nude athymic mice. After intra-peritoneal injection, animals develop metastatic spread similar to that of clinical ovarian cancer. Disease progression is characterized by development of massive ascites production, extensive intra-peritoneal tumours and pulmonary metastases. The malignant ascites cells express the ovarian cancer associated antigen CA-125. The mouse model exhibits histopathological and embryological features consistent with human ovarian cancer, a reproducible pattern of metastases which parallels the human disease, suitable markers for following response to treatment, and drug sensitivity profiles similar to those of human ovarian cancer (Hamilton et al., 1984).

OVCAR-3 cells ($13 \times 10^6$) cultured in vitro were injected subcutaneously into nude mice. Eight weeks later tumours were dissected, minced and washed ×3 in PBS. The cultured cells were suspended in 0.3% of Bacto agar in RPMI supplemented with 20% horse serum, penicillin (100 u/ml) streptomycin (2 mg/ml) and insulin 3 u/ml, EGF 100 ng/ml, asparagine (0.1 mg/ml) and DEAE dextran 0.5 mg/ml to yield a cell density of $5 \times 10^6$ cells per ml. 2-mercaptoethanol was added at a concentration of 50 μM just before cells were plated. A portion (1 ml) of the resultant mixture was added onto a feeder layer which combined 0.2 ml of medium conditioned by adherent spleen cells of mineral oil-primed BALB/c mice in 0.5% Bactoagar. Cultures were incubated at 37° C. in 5% $CO_2$. At 5 day intervals, 0.8 ml of growth medium with EGF (10 ng/ml) was layered onto the agarose surface. After 3 weeks, colonies of cells were harvested in mass and plated in 75 cm2 flasks. These cells were then injected subcutaneously into mice. $50 \times 10^6$ tumour cells harvested from these subcutaneously tumours were suspended in 1 ml of medium and injected intra-peritoneally into each carrier nude mouse. Ascites fluid was collected, washed with sterile saline, and centrifuged at 300 g and 4° C. for 5 minutes.

$10 \times 10^6$ viable tumour cells collected from the ascites fluid and suspended in 1.0 ml of medium (RPMI 1640) were injected intra-peritoneally into each test animal. For all experiments, 6-8 weeks old nude female athymic Balb c nu/nu mice (Animal Resources Centre, Perth, Western Australia) were used as test animals. These animals were housed in pathogen-free isolated conditions in the Biological Resources Centre of the University of New South Wales and were fed autoclaved pellets and water ad libitum. The general health of the animals was checked daily. All protocols used were approved by the University of New South Wales Animal Ethics Committee.

Mice inoculated intra-peritoneally as described above were randomly distributed into either the albendazole treated or control groups. Drug treatment was initiated (×3 weekly for 4 weeks).

Albendazole suspended in 0.5% carboxymethylcellulose was administered at a dose of 150 mg/kg to all treated animals. For oral administration, a suspension of 15 mg/ml was prepared (0.1 ml/10 g body weight) while for intra-peritoneal treatments a suspension of 3 mg/ml was used (3 mg/1 ml/20 g mice).

Figure 2:
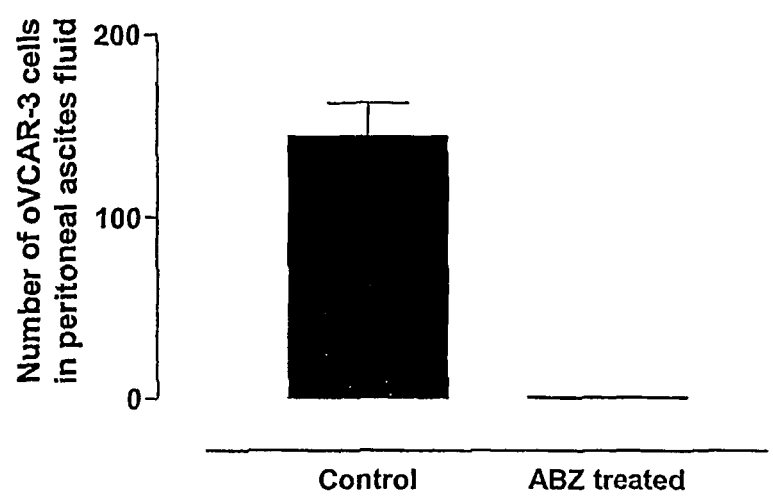
FIG. 2. Effect of albendazole on the number of OVCAR-3 cells present in peritoneal ascites fluid aspirated from tumour-bearing nude mice. Each value represents the mean±s.e. of 6 to 8 determinations.

Immediately prior to euthanasia, animals were anaesthetised with pentobarbitone, and blood samples were collected through cardiac puncture. Animals were then euthanized by an overdose of the anaesthetic drug. For collection of the ascites fluid, 2 ml of physiological saline was injected intra-peritoneally and the contents of the peritoneal cavity were mixed by kneading. Peritoneal fluid was then recovered, its volume recorded (FIG. 1) and the number of viable tumour cells present counted (FIG. 2). Plasma and cell-free ascites fluid were stored at −80° C. for subsequent analysis.

Figure 3:
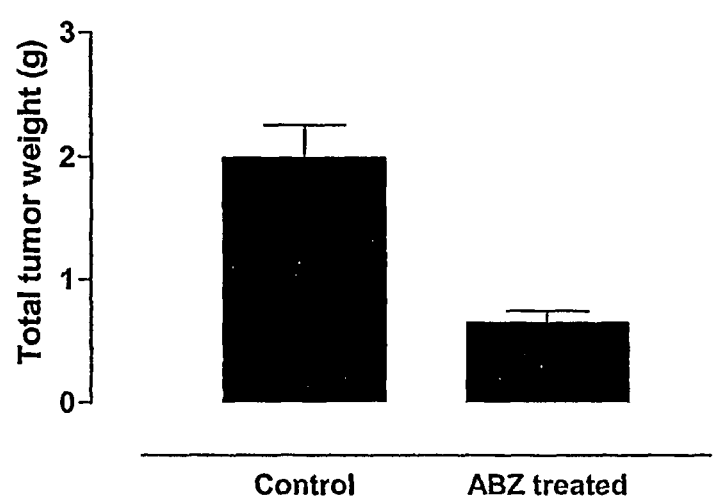
FIG. 3. Effect of albendazole on total weight of peritoneal tumours from nude mice. Each value represents the mean±s.e. of 6 to 8 determinations.
Figure 4:
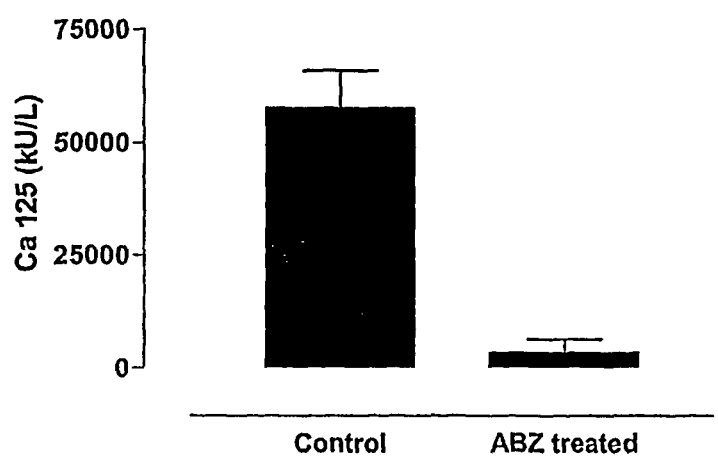
FIG. 4. Effect of albendazole on CA-125 levels in OVCAR-3 tumour-bearing from nude mice. Each value represents the mean±s.e. of 6 to 8 determinations.
Figure 5:
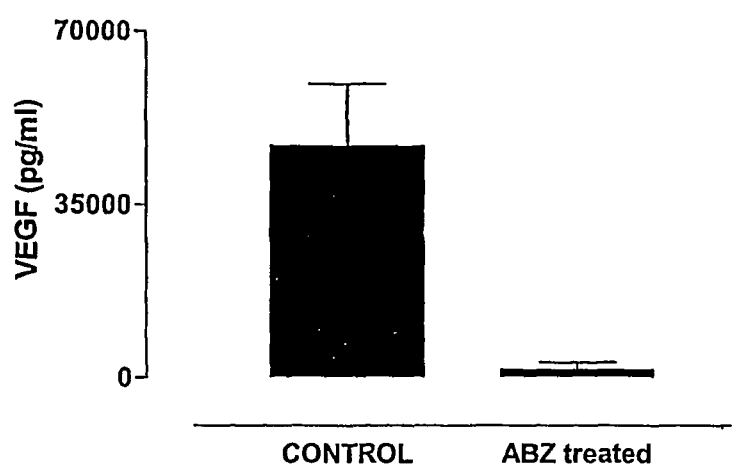
FIG. 5. VEGF levels in the peritoneal fluid of nude mice bearing peritoneal OVCAR-3 tumours. Each value represents the mean±s.e. of 6 to 8 determinations.
Figure 6:
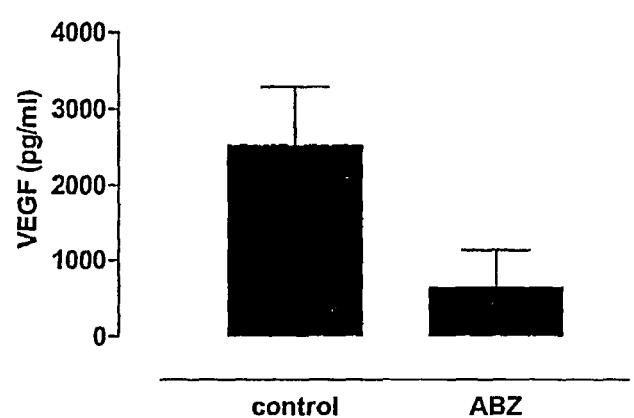
FIG. 6. Effect of albendazole on plasma VEGF levels in nude mice bearing OVCAR-3 tumours. Each value represents the mean±s.e. of 6 to 8 determinations.

Tumours present in the peritoneal cavity were dissected, weighed (FIG. 3) and stored for subsequent analysis. Animals were also checked for the presence of metastasis in lung, liver, spleen, stomach and pancreas (data not shown). Tumour marker (CA-125) levels (FIG. 4) were analyzed by St George Hospital Biochemistry laboratories. VEGF concentrations in ascites fluid (FIG. 5) and plasma (FIG. 6) were determined using Elisa kits (Quantikine R& D systems).

The results obtained demonstrate that in OVCAR-3 tumour bearing mice intra-peritoneal albendazole treatment leads to dramatic reductions in ascites volume and VEGF levels.

VEGF Isoforms

OVCAR-3 cells isolated from ascites fluid of nude mice bearing tumours (as described above) were examined for the expression of mRNA for various VEGF isoforms ($VEGF_{121}$, $VEGF_{165}$, $VEGF_{189}$, $VEGF_{206}$) by RT-PCR. Cells were separated through centrifugation (5 min at 1500 rpm) and total RNA was isolated from the remaining cell-pellet by using the High Pure RNA Isolation Kit (Roche Diagnostics Corporation) according to the manufacturer's protocol. The RNA concentration was measured in a spectrophotometer at the wavelength of 260 nm using a Quartz Spectrophotometer Cell (BioRad).

Primers for amplification of VEGF were constructed on the basis of the sequences presented in Pellizzaro et. al 2002; VEGF sense: 5'-CAC ATA GGA GAG ATG AGC TTC-3' (SEQ ID NO:1); VEGF antisense: 5'-CCG CCT CGG CTT GTC ACA T-3' (SEQ ID NO:2). These primers amplify the following products: 100 bp for $VEGF_{121}$, 230 bp for $VEGF_{165}$, 300 bp for $VEGF_{189}$ and 320 bp for $VEGF_{206}$. The β-Actin gene was used as an internal control (202 bp) using primers as follows: β-Actin sense: 5'-CTT CCT GGG CAT GGA GTC CT-3' (SEQ ID NO:3); β-Actin antisense: 5'-GGA GCA ATG ATC TTG ATC TT-3' (SEQ ID NO:4) (Marchini et. al. 1996).

250 ng/50 ng of total RNA was used to amplify VEGF/β-Actin using the SuperScript™One Step RT-PCR with Platinum®Taq (Invitrogen). RNA was diluted with DEPC treated water to a final volume of 11 µl for one RT-PCR reaction. 12.5 µl 2×Reaction Mix (final concentration 1×), 1 µl Primer Mix (40 µl DEPC-water, 5 µl 100 µM Sense Primer, 5 µl 100 µM Antisense Primer; final Primer-concentration 0.2 µM) and 0.5 µl RT/Platinum®Taq were added to the RNA dilution (total volume of one reaction=25 µl). To keep the enzymes (RNAse & Taq) inactive all pipette-steps were performed on ice. The amplification was carried out in a Palm Cycler (Corbett Research) after an initial cDNA synthesis at 54° C. for 30 min and 5 min at 94° C. for denaturation. This was followed by 27 cycles (denaturation at 94° C. for 1 min, primer annealing at 60° C. for 1 min, primer extension at 72° C. for 45 s) and a final extension of 72° C. for 10 min.

Figure 7:
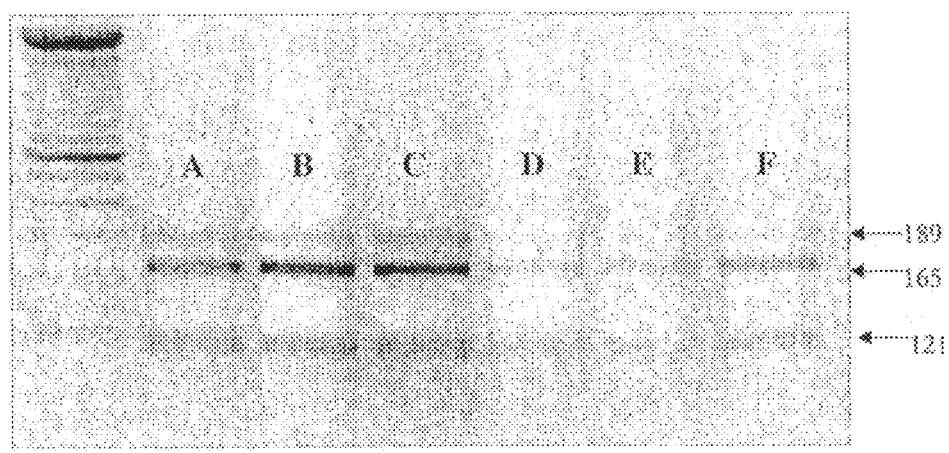
FIG. 7. RT-PCR presenting various VEGF mRNA isoforms extracted from cells aspirated from ascites fluid or peritoneal wash of nude mice bearing peritoneal OVCAR-3 tumours. A-C are cells from control animals, while, D-F were extracted from albendazole treated intraperitoneally (150 mg/kg×3 weekly for 4 weeks) animals.

The RT-PCR products were visualized by electrophoresis (25 min at 120V) on 2% agarose gel in 1×TAE buffer containing ethidium bromide. To quantify the size of the products a 100 bp DNA ladder (Invitrogen) was run with the samples. The results are shown in FIG. 7 which demonstrates that intra-peritoneal albendazole administration led to a significant reduction in the expression of VEGF mRNA.

Example 2

Effect of Albendazole on In Vitro VEGF Secretion

SKOV-3 human cystadenocarcinoma cell line, obtained from the American Type Culture Collection (ATCC Accession No. HTB 77) were grown in McCoy's 5a medium with 1.5 mM L-glutamine, 100 units/ml penicillin, and 100 µg/ml streptomycin, supplemented with 10% FCS. Cells were grown to confluence and harvested by trypsinization with 0.25 mg/ml trypsin/EDTA and suspended in the medium before plating. These were then seeded ($2 \times 10^5$) on plastic 6-well Corning culture plates. Cultures were maintained in a 37° C. incubator in a humidified atmosphere of 95% O2/5% $CO_2$. Twenty-four hours later, the medium was removed. Subconfluent cultures were washed three times with phosphate buffer followed by incubation for 6 hours with culture medium containing various concentrations of albendazole (0, 0.1, 0.25 and 1.0 µM) dissolved in 1% ethanol. After completion of the treatment period, medium from the wells were individually collected and analysed for the VEGF concentration using an enzyme-linked immunosorbant assay (ELISA) that detects soluble $VEGF_{121}$ and $VEGF_{165}$ isoforms (Quantikine R&D systems, Minneapolis, USA).

In another set of experiments, while keeping all other conditions constant, the matrix metalloproteinase MMP-9 (6 ng/ml) was used to stimulate cells to increase VEGF production prior to treatment with albendazole. There is evidence that MMP-9 induces the release of biologically active VEGF in the culture medium of ovarian tumour cells and in ascites of ovarian tumour-bearing mice (Belotti et al., 2003). SKOV-3 cells were exposed to the recombinant activated form of MMP-9, which was directly added to the cell culture medium containing various concentrations of albendazole.

Figure 8:
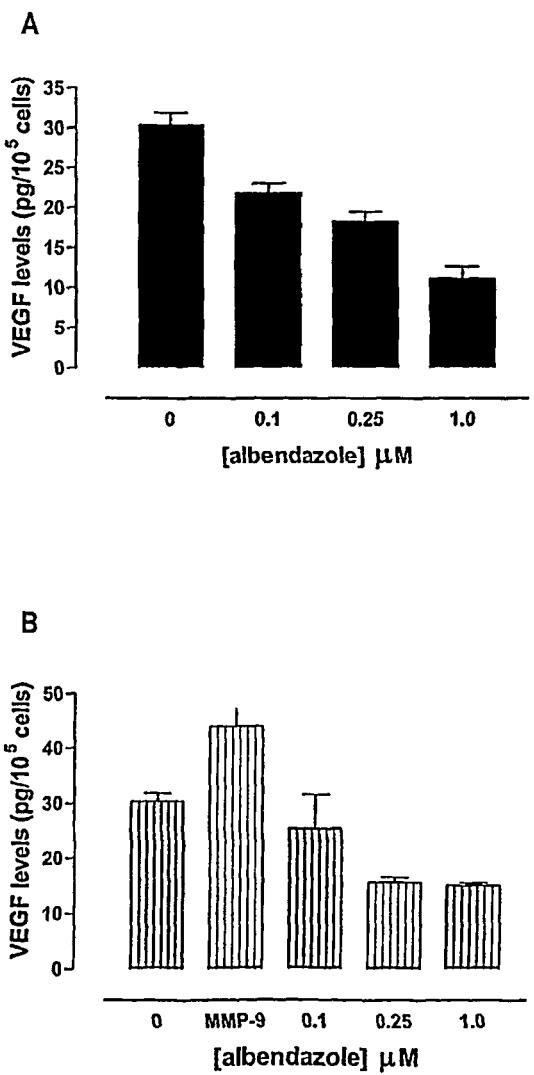
FIG. 8. Effect of 6 hour albendazole treatment on VEGF production in SKOV-3 cells in vitro. Each value represents the mean±s.e of 4 determinations. A. VEGF levels (pg/$10^5$ cells) in the presence of varying concentrations (µM) of albendazole. B. VEGF levels (pg/$10^5$ cells) in the presence of varying concentrations (µM) of albendazole following co-treatment with 6 ng/ml MMP-9.

Results obtained for both sets of experiments are presented in FIG. 8. It is clear from these results that treatment of SKOV-3 cells (which constitutively release VEGF) with various concentrations of albendazole leads to dose-dependent reduction in VEGF secretion. Using a haemocytometer and Trypan blue exclusion method, viability of cells present in each well was checked (at the end of the treatment period) and the VEGF concentration calculated as picograms per $10^5$ cells. Although due to the antiproliferative action of albendazole, cells could not be incubated for longer than 6 hours, a dose-dependent reduction in VEGF concentration was observed. In the absence of MMP-9, at the highest albendazole concentration used (1.0 µM), VEGF concentration were reduced by 64% (FIG. 8A). Stimulation of cells with MMP-9 led to a 44.8% increase in VEGF concentration in 6 hours (FIG. 8B). Albendazole treatment of MMP-9 stimulated cells led to profound reduction in VEGF concentrations; VEGF concentrations in the 1 µM albendazole treated cells were reduced by 65%. In these cells and under the described conditions, 0.1 µM albendazole blocked the excess VEGF secretion induced by MMP-9 stimulation.

These results clearly show that albendazole profoundly reduces VEGF secretion from SKOV-3 human ovarian cancer cells in vitro.

Example 3

Inhibition of Neovascularisation in a Murine Model of Proliferative Retinopathy

The ability of albendazole to serve as a potential inhibitor of age-related macular degeneration (AMD) was evaluated in a well-established murine model of retinal neovascularisation, ROP (retinopathy of prematurity), relevant to AMD.

The experiments described below were approved by the UNSW Animal Care and Ethics Committee.

Postnatal day 6 (P6) C57BL/6 mice were exposed to hyperoxic (75% oxygen) for 4 days in Quantum-Air Maxi-Sealed cages (Hereford, UK). P10 mice were returned to normoxia, anaesthetized (17 mg/kg ketamine and 2.5 mg/kg xylazine) and bolus intravitreal injections of volume 2 µl, containing 0.1, 1 or 10 µg albendazole in DMSO; DMSO alone or 1×PBS alone were administered using a 26 gauge beveled needle attached to a micro syringe (SGE International, Melbourne, Australia). Mice remained at room oxygen for a further 7 days then eyes were removed and fixed in 10% formalin/PBS. Serial cross sections (50 microns) were stained with haematoxylin and eosin. Blood vessels from each, group were counted under light microscopy (400×) and expressed as the mean±SEM.

Figure 9:
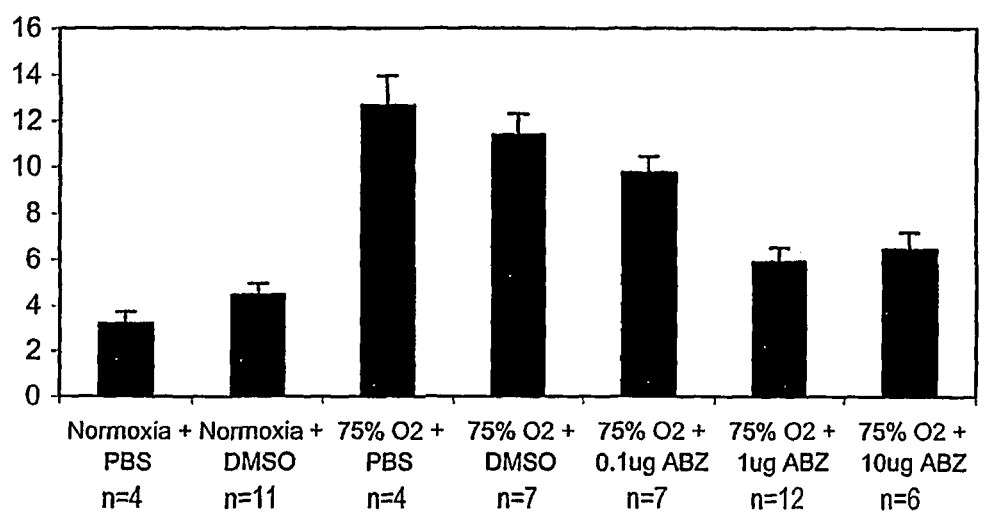
FIG. 9. Retinal neovascularisation (blood vessel count) in mice under normoxic and hyperoxic (75% $O_2$) conditions following treatment with DMSO, PBS or varying concentrations of albendazole (0.1 µg, 1 µg or 10 µg in 2 µl).

As shown in FIG. 9, hyperoxia-normoxia produced a 2-3-fold increase in retinal neovascularisation. Albendazole significantly inhibited hyperoxia-induced retinal angiogenesis following single intravitreal injection of the drug. Inhibition was dose-dependent and observed with amounts as little as 1 ug. DMSO alone (the albendazole vehicle) did not affect blood vessel formation in hyperoxia-exposed mice, with blood vessel counts not different from those in the PBS group.

Statistical analysis of the results shown graphically in FIG. 9 was performed using a 2-tailed Student's t-test with unequal variance (Table 1).

TABLE 1

| Statistical significance of albendazole treatment | |
|---|---|
| DMSO v 10 ug albendazole | P = 0.000651889 |
| DMSO v 1 ug albendazole | P = 0.000117785 |
| DMSO v 0.1 ug albendazole | P = 0.305488779 |
| 1 ug v 10 ug albendazole | P = 0.654672771 |
| 1 ug v 0.1 ug albendazole | P = 0.0000853701 |

Figure 10:
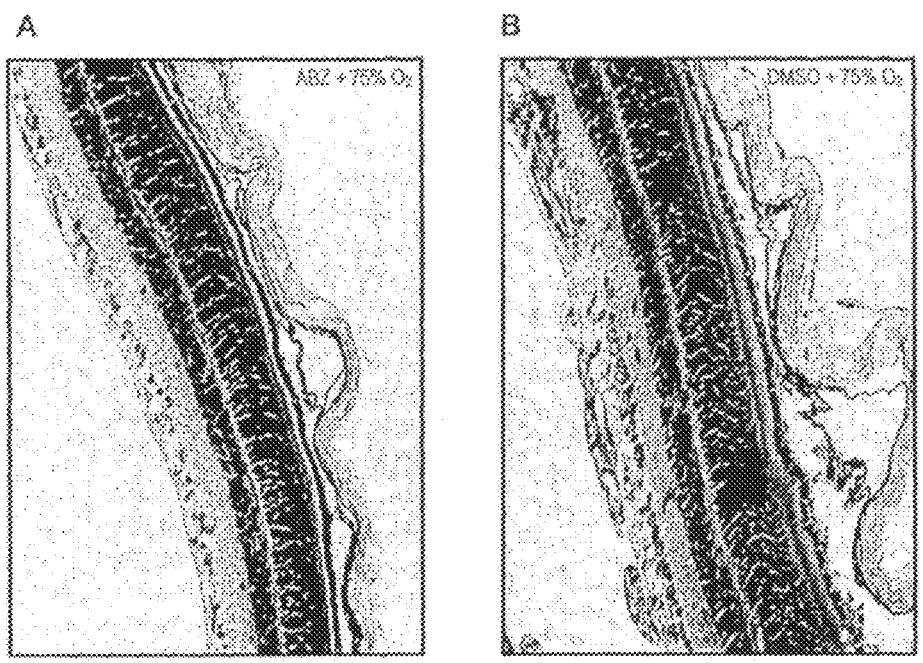
FIG. 10. Light micrographs of haematoxylin and eosin stained cross sections (50 µm) of mouse retinas following injection with albendazole in DMSO (A) or DMSO alone (B).

Haematoxylin and eosin stained sections (FIG. 10) revealed that there was no detectable morphological difference between the DMSO alone injected group (FIG. 10B) and the albendazole+DMSO injected group (FIG. 10A), other than neovascularisation, suggesting that, within the confines of this study, no adverse or toxic reaction towards albendazole and/or its vehicle, DMSO.

Example 4

Compositions for Treatment

In accordance with the best mode of performing the invention provided herein, specific compositions are outlined below. The following are to be construed as merely illustrative examples of compositions and not as a limitation of the scope of the present invention in any way.

Example 4(A)

Composition for Parenteral Administration

A composition for parenteral injection could be prepared to contain 0.05 mg to 5 g of a compound of formula I (such as albendazole) in 10 mls to 2 litres of 1% carboxymethylcellulose.

Similarly, a composition for intravenous infusion may comprise 250 ml of sterile Ringer's solution, and 0.05 mg to 5 g of a compound of formula I.

A composition suitable for administration by injection may also be prepared by mixing 1% by weight of the compound in 10% by volume propylene glycol and water. The solution can be sterilised by filtration.

Example 4(B)

Composition for Oral Administration

A composition of a compound of formula I in the form of a capsule may be prepared by filling a standard two-piece hard gelatin capsule with 500 mg of the compound, in powdered form, 100 mg of lactose, 35 mg of talc and 10 mg of magnesium stearate.

Example 4(C)

Composition for Topical Administration

A typical composition for delivery as a topical ointment includes 1.0 g of a compound of formula I, together with white soft paraffin to 100.0 g, dispersed to produce a smooth, homogeneous product.

Example 4(D)

Eye Drop Composition

A typical composition for delivery as an eye drop is outlined below:

| | |
|---|---|
| Suitbale compound | 0.3 g |
| Methyl Hydroxybenzoate | 0.005 g |
| Propyl Hydroxybenzoate | 0.06 g |
| Purified Water about to | 100.00 ml. |

The methyl and propyl hydroxybenzoates are dissolved in 70 ml purified water at 75° C., and the resulting solution is allowed to cool. The compound is then added, and the solution sterilised by filtration through a membrane filter (0.22 μm pore size), and aseptically packed into sterile containers.

References

Belotti, D., Paganoni, P., Manenti, L., Garofalo, A., Marchini, S., Taraboletti, G., and Giavazzi, R. Matrix metalloproteinases (MMP9 and MMP2) induce the release of vascular endothelial growth factor (VEGF) by ovarian carcinoma cells: implications for ascites formation. Cancer Research., 63: 5224-5229, 2003.

Burbridge, M. F., Kraus-Berthier, L., Naze, M., Pierre, A., Atassi, G., and Guilbaud, N. Biological and pharmacological characterisation of three models of human ovarian carcinoma established in nude mice: use of the CA125 tumor marker to predict antitumour activity. International Journal of Oncology., 15: 1155-1162, 1999.

Dvorak, H. F., Brown, L. F., Detmar, M., and Dvorak, A. M. Vascular permeability factor/vascular endothelial growth factor, microvascular hyperpermeability, and angiogenesis. American Journal of Pathology., 146: 1029-1039, 1995.

Hamilton, T. C., Young, R. C., Louie, K. G., Behrens, B. C., McKoy, W. M., Grotzinger, K. R., and Ozols, R. F. Characterization of a xenograft model of human ovarian carcinoma which produces ascites and intraabdominal carcinomatosis in mice. Cancer Research., 44: 5286-5290, 1984.

Hasumi, Y., Mizukami, H., Urabe, M., Kohno, T., Takeuchi, K., Kume, A., Momoeda, M., Yoshikawa, H., Tsuruo, T., Shibuya, M., Taketani, Y., and Ozawa, K. Soluble FLT-1 expression suppresses carcinomatous ascites in nude mice bearing ovarian cancer. Cancer Research., 62: 2019-2023, 2002.

Marchini, S., Codegoni, A. M., Bonazzi, C., Chiari, S., and Broggini, M. Absence of deletions but frequent loss of expression of p16INK4 in human ovarian tumours. British Journal of Cancer., 76: 146-149, 1997.

Ozols, R. F., Willson, J. K., Weltz, M. D., Grotzinger, K. R., Myers, C. E., and Young, R. C. Inhibition of human ovarian cancer colony formation by adriamycin and its major metabolites. Cancer Research., 40: 4109-4112, 1980.

Pellizzaro, C., Coradini, D., and Daidone, M. G. Modulation of angiogenesis-related proteins synthesis by sodium butyrate in colon cancer cell line HT29. Carcinogenesis., 23: 735-740, 2002.

Smith, E. M. and Jayson, G. C. The current and future management of malignant ascites. Clinical Oncology (Royal College of Radiologists). 15: 59-72, 2003.

Xu, L., Yoneda, J., Herrera, C., Wood, J., Killion, J. J., and Fidler, I. J. Inhibition of malignant ascites and growth of human ovarian carcinoma by oral administration of a potent inhibitor of the vascular endothelial growth factor receptor tyrosine kinases. International Journal of Oncology., 16: 445-454, 2000.

Zebrowski, B. K., Liu, W., Ramirez, K., Akagi, Y., Mills, G. B., and Ellis, L. M. Markedly elevated levels of vascular endothelial growth factor in malignant ascites. Annals of Surgical Oncology., 6: 373-378, 1999a.

Zebrowski, B. K., Yano, S., Liu, W., Shaheen, R. M., Hicklin, D. J., Putnam, J. B., Jr., and Ellis, L. M. Vascular endothelial growth factor levels and induction of permeability in malignant pleural effusions. Clinical Cancer Research., 5: 3364-3368, 1999b.

The invention claimed is:

1. A method for treating malignant ascites caused by ovarian cancer in a subject, the method comprising administering to the subject, who is suffering from malignant ascites caused by ovarian cancer, an effective amount of an albendazole wherein the effective amount is in the range of about 10 mg to about 200 mg per kg body weight per 24 hours, and wherein the administration is intracavitary.

2. The method of claim 1, wherein the intracavitary administration is intraperitoneal or intrapleural.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: Synthetic primer - VEGF sense

<400> SEQUENCE: 1
cacataggag agatgagctt c                                              21

<210> SEQ ID NO 2
<211> LENGTH: 19
<212> TYPE: DNA
<213> ORGANISM: Artificial
<220> FEATURE:
<223> OTHER INFORMATION: Synthetic primer - VEGF antisense

<400> SEQUENCE: 2
ccgcctcggc ttgtcacat                                                 19

<210> SEQ ID NO 3
<211> LENGTH: 20
<212> TYPE: DNA
<213> ORGANISM: Artificial
<220> FEATURE:
<223> OTHER INFORMATION: Synthetic primer - beta-Actin sense

<400> SEQUENCE: 3
cttcctgggc atggagtcct                                                20

<210> SEQ ID NO 4
<211> LENGTH: 20
<212> TYPE: DNA
<213> ORGANISM: Artificial
<220> FEATURE:
<223> OTHER INFORMATION: Synthetic primer - beta-Actin antisense

<400> SEQUENCE: 4
ggagcaatga tcttgatctt                                                20